United States Patent [19]

Sharples

[11] Patent Number: 4,686,752

[45] Date of Patent: Aug. 18, 1987

[54] METHOD OF FORMING SLOTS IN A MATERIAL-RETAINING PLATE FOR A PACKED COLUMN REACTOR IN AN ANALYTICAL INSTRUMENT

[75] Inventor: Thomas D. Sharples, Atherton, Calif.

[73] Assignee: Beckman Instruments, Inc., Fullerton, Calif.

[21] Appl. No.: 734,626

[22] Filed: May 12, 1985

Related U.S. Application Data

[62] Division of Ser. No. 628,928, Jul. 9, 1984, abandoned.

[51] Int. Cl.[4] ............... B23P 15/16; B23P 17/00; B21D 28/00
[52] U.S. Cl. ..................... 29/163.5 R; 29/423; 29/424; 72/47; 72/335
[58] Field of Search ............. 29/157 C, 163.5 R, 423, 29/424; 72/46, 335, 379, 324, 47; 33/168 R, 168 B

[56] References Cited

U.S. PATENT DOCUMENTS

| | | | | |
|---|---|---|---|---|
| 2,041,553 | 5/1936 | Larsen | .................. | 261/95 X |
| 2,492,380 | 12/1949 | Duma | .................. | 33/168 R |
| 3,063,142 | 11/1962 | Kroon | .................. | 29/424 |
| 3,279,043 | 10/1966 | Wirt | .................. | 29/424 X |
| 3,534,856 | 10/1970 | Marsh | .................. | 210/498 |
| 3,603,129 | 9/1971 | Williams et al. | .................. | 72/324 |
| 3,818,667 | 6/1974 | Wagner | .................. | 422/311 X |

FOREIGN PATENT DOCUMENTS 152423 2/1938 Austria ............... 33/168 R

Primary Examiner—E. Michael Combs
Attorney, Agent, or Firm—Steven R. Markl; P. R. Harder; William H. May

[57] ABSTRACT

A slotted retaining plate for use in a tubular reactor within an analytical system. The reactor contains inert packed material which provides for the necessary flow path length for a fluid stream entering the reactor. The retaining plate is extremely thin and has an array of slots which permit the necessary flow of the stream through the reactor, but retain the packing material within the reactor. The design of the slot array in the retaining plates essentially eliminates any possible impediment to the stream flow. The slots are adjustable to provide more flexibility in slot size control to allow use of smaller packing particles within the reactor and improve the instrument resolution in, for example, an amino acid analyzer.

4 Claims, 10 Drawing Figures

METHOD OF FORMING SLOTS IN A MATERIAL-RETAINING PLATE FOR A PACKED COLUMN REACTOR IN AN ANALYTICAL INSTRUMENT This is a division of application Ser. No. 628,928, filed July 9, 1984, now abandoned.

BACKGROUND OF THE INVENTION

The present invention is directed to automated analyzer systems and, more specifically, is directed to a retaining plate or disc used within a reactor of an automated analyzer system wherein the plate permits ingress or egress of a fluid stream through the reactor while retaining packing material within the reactor. A color development reactor in the detection system of an amino acid analyzer has been selected as a representative application.

In some amino acid analyzers, a very small or micro chromatographic column is used as a specialized application of a liquid column chromatographic separation technique, utilizing ion exchange resin as the stationary phase and eluting buffers of varying pH and salt concentration as the moving phase. Amino acids contained in a sample are introduced at the top of the column and are separated from each other as they are eluted through the resin bed which comprises the column packing. For amino acid analysis, the method for detecting the amino acids in the effluent stream has been to combine the column effluent with a reagent that is metered into the stream at a flow rate proportionally to that of the column eluent. When the reagent combines with the amino acids present in the stream, compounds are formed which, when subjected to further development process, can be detected by specific changes in optical properties such as absorption or fluorescence.

One of the classical detection methods in amino acid analyzer systems is that developed by Spackman and Moore, wherein the reagent used is ninhydrin dissolved in a suitable solvent/buffer solution. Under this process, the column effluent/reagent solution is heated in a reactor to a fixed temperature for a specified period of time. The compound developed as a result of this process will have specific colors, the intensities of which are proportional to the amounts of compounds contained in the flowing stream. The optical density of these compounds is measured at specific wavelengths.

Important to the calibration of the analyzer in terms of its specific sensitivity to detect amino acids is that the fluid/reagent mixture be maintained at a constant elevated temperature for a fixed period of time. It is critical to the stability of the instrument calibration that the two parameters of temperature and exposure time remain constant during the color development process. Classically, this has been accomplished by causing the effluent to pass through a TFE Teflon capillary coil which is normally suspended in a boiling water bath to act as the reactor in the amino acid analyzer system.

The separation techniques employed in early analyzers required several hours to complete a single analysis. In such systems, it became common practice to retain the flowing stream within the reactor for as long as fifteen minutes to complete the color development. Newer techniques have increased the performance of these analyzers to permit the same analyses to be completed in the order of twenty minutes. It has then become necessary to provide increased color development in a much shorter period of time. Reference is made to FIG. 1 showing empirical results of studies which relate the optical densities of compounds formed by mixtures of ninhydrin and amino acids as a function of development time and temperature.

Although many prior arrangements have used the design of TFE Teflon capillaries immersed in boiling water to obtain the necessary reactor temperatures, more recent approaches have envisioned the use of an elongated straight tube or column which is packed with inert material having a small particle size. This reactor tube can be heated by a variety of approaches, including placing the reactor on a thermoconductive block to which is attached a thermoelectric module, which operates in conjunction with a heat sink. By proper control of the operation of the thermoelectric module, the reactor can operate significantly above 100° C. without damage to the apparatus or the stream being analyzed. The temperature control apparatus for the reactor using a thermoelectric module can maintain a temperature as high as 150° C. with a capability of controlled cooling, as well as rapid cooldown in the case of power loss to the system.

One of the necessary elements in a reactor that is packed with small inert material such as diamond particles (approximately 0.002 inch diameter) is a retaining plate or disc positioned at each end of the reactor to properly retain the extremely small particles within the reactor while allowing for the requisite flow of the stream in and out of the reactor. The retention of the particles within the reactor is very important, since it is necessary for the successful operation of the analyzer to avoid any excess voids or space in the diamond packing. One approach in the design of a retaining plate used in a reactor for an amino acid analyzer has been to perforate the plate with a plurality of possibly six or eight holes each having a diameter of less than 0.002 inches. Because of the corrosive content of the stream flowing through the analytical system, platinum has been used for the plate having a thickness of approximately 0.003 inches. Consequently, it is exceedingly difficult and expensive to place the necessary number of holes with the critical diameter in the thin platinum plate.

One concern with respect to the use of a plurality of single holes in a thin disc or plate is possible occurrences of plugging of these holes which could result in serious problems, since the system is operating at high pressure and could result in damage to pressure gauges.

Another problem with respect to utilizing a plurality of single holes in the plate is the fact that holes any smaller than 0.002 inches in diameter may accentuate the reactor plugging problem. However, it is desirable to use particles in the packing of the reactor having a size no larger than 80 microns. Within limits, smaller sizes will improve the instrument resolution.

Although one approach to possible solution for reactor plugging is to place many more holes in the retaining plate, the cost of piercing additional holes in a thin plate made of a material such as platinum is high.

SUMMARY OF THE INVENTION

The generally cylindrical elongated tube used as a heated reactor in an automated analyzer is packed with an inert material having a small particle size (70–80 microns or less) of limited-size distribution. The packing ensures the uniform fluid velocity across a section of the reactor and, hence, avoids the problem of laminar flow with its degrading effects on the resolution of the analyzer.

When operating a color development reactor in an amino acid analyzer at temperatures above 100° C., the choice of materials that are able to withstand such high temperatures and the range of pH involved is essentially limited to the use of noble metals, certain precious metal alloys and possibly a few difficult-to-fabricate exotic alloys. Consequently, the use of a straight elongated tube that is internally plated with or possibly constructured from a noble metal will provide a highly desirable reactor for use at high temperature. Also, the configuration of the tube packed with an inert material provides a device which can be fabricated at a price considerably below that of typically used capillary tubes, which would have to be made of a suitable noble metal material.

The present invention is directed to the retaining plates that are used on each end of the reactor tube to establish the entry and exit ports for the fluid stream entering and leaving the reactor. As stated previously, because of the temperature and the pH of the flowing stream, the retaining plates must be made of a material such as platinum and are very thin, approximately 0.003 inches. The retaining plates of the present invention have an array of offset slots. These slots are readily sized to be compatible with the size of the particles being packed in the tubular reactor, so that the escape of any of the particles from the reactor chamber will be prevented. Furthermore, the array of offset slots is equivalent to a great number of holes within the plate. Consequently, the problem of plugging or impediment to the stream flow is essentially eliminated.

By using the offset slot configuration, it is possible to adjust the width or size of the slots to accommodate smaller particles used in the packing of the reactor. This is an advantage, since instrument resolution is improved by using, within limits, smaller particles. The aspect of forming offset slots in the thin platinum plate presents a much more efficient and economically feasible approach for providing openings at each end of the reactor to allow the desired flow of the stream through the system.

DETAILED DESCRIPTION OF THE INVENTION

For exemplary purposes, the application of the present invention will be discussed with respect to its use in an amino acid analyzer system. In such a system it is necessary to control the temperature of the thermal reactor to provide desirable color development relating to the flowing stream.

Figure 2:
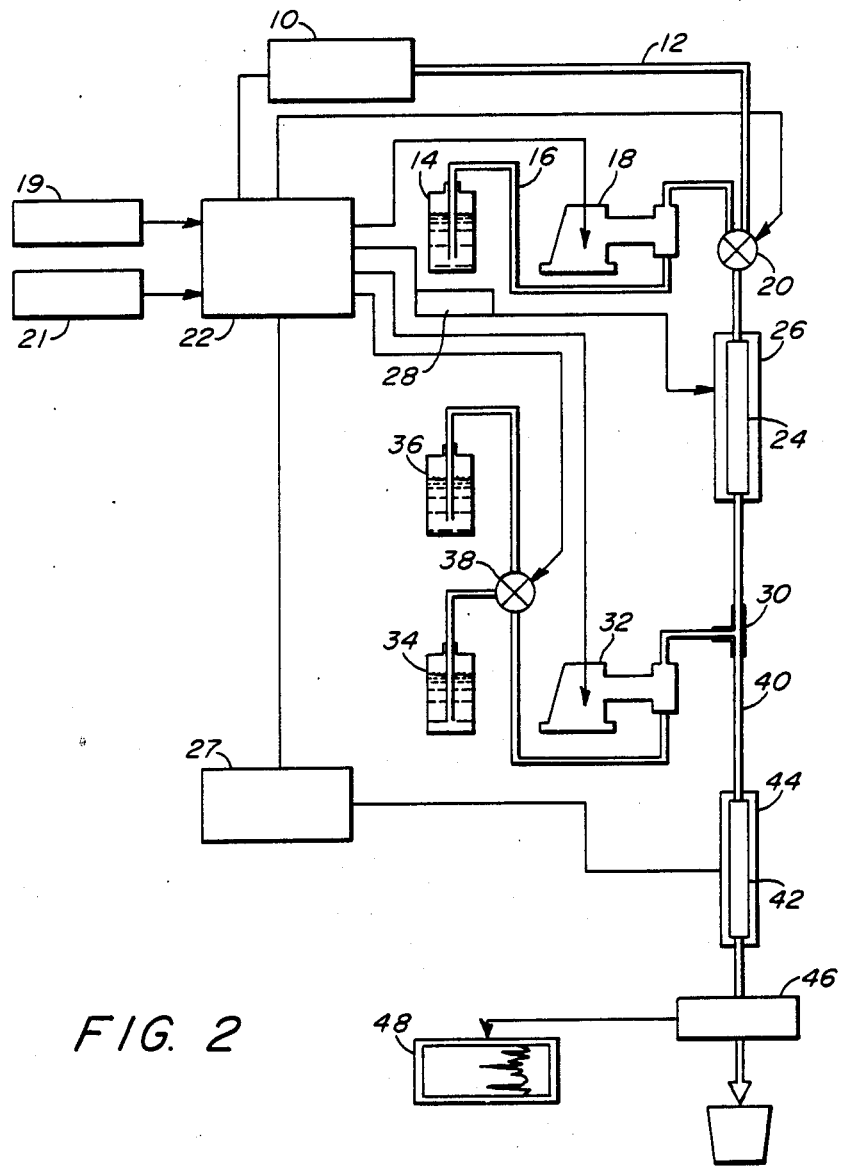
FIG. 2 is a schematic diagram of an overall amino acid analyzer system.

Attention is directed to FIG. 2, showing a schematic view of an overall amino acid analyzer system. A sample table 10 receives the various samples for introduction into the automated system which are sequenced through the conduit 12 to the sample injector valve 20. An eluting buffer 14 is transferred through the conduit 16 by the buffer pump 18 into the sample injector valve 20. The sample injector valve 20 is automatically operated by the analyzer controller 22 in order to sequence the sample in conjunction with the eluting buffer for introduction into the chromatographic column 24. As explained previously in the Background of the Invention, the liquid column chromatographic separation technique uses an ion exchange resin as a stationary phase with eluting buffers of varying pH and salt concentration as the moving phase. The resin base is packed into the column 24 for receipt of the eluting buffer in conjunction with the sample. The column 24 has a temperature regulator apparatus 26. A control system 28 is utilized to regulate the temperature in the column 24.

After the eluting stream exits the bottom of the column 24, it enters into a mixing tee 30 which is in fluid communication with a reagent pump 32 that is designed to pump the reagent 34 into the mixing tee 30. A solvent 36 is also used by operation of the valve 38 to pump solvent into the system which is done during shutdown procedures.

The reagent mixture with the eluting buffer 14 from the liquid chromatographic column 24 flows through the conduit 40 into the reactor 42. The compounds produced by the reagent mixing with the amino acids from the sample are subjected to further development in the reaction chamber of the reactor where the mixed flowing stream is heated to a specific temperature for a specific time. The presence of these compounds is detected by noting specific changes in optical properties of the stream. The optical density at specific wavelengths will indicate the amounts of compounds present in the flowing stream. The photometer 46 is used to observe these colors and intensities while the recorder 48 provides a documented record.

A control system 28 is utilized to regulate the temperature in the column 24 while another control system 27 regulates the temperature in the reactor 42. The analyzer controller operates the two temperature control systems 27 and 28. Inputs to the analyzer controller 22 are from the operator entered program parameters 19 or from the analyzer alarm monitor 21. Sensors within the analyzer system provide information to the alarm monitor of possible conditions where the stream within the reactor may be subject to boiling. If these types of conditions occur, the temperature of the reactor is immediately cooled.

Figure 1:
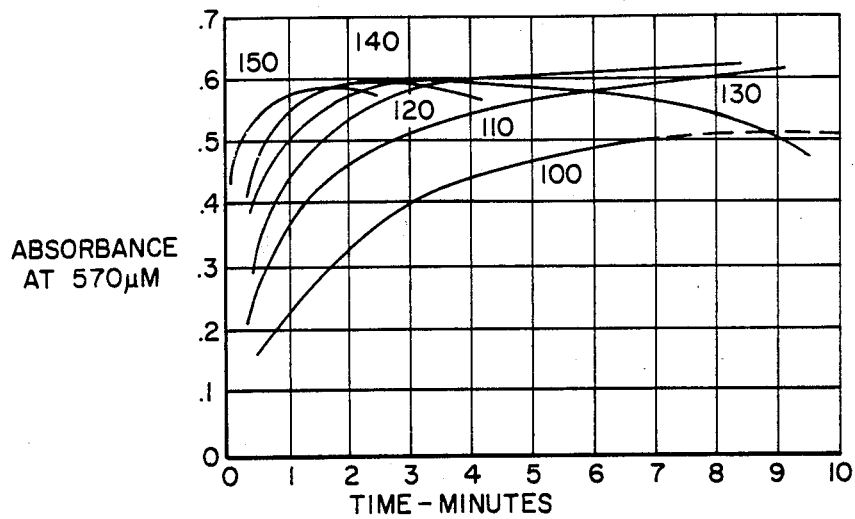
FIG. 1 is a graphic representation of color development of mixtures of amino acids and ninhydrins for variations in temperature and time.

Reference is made to FIG. 1 showing the results of some empirical studies made of the color development produced in ninhydrin/amino acid compounds under varying conditions of time and temperature. The graphical representation in FIG. 1 is a plot of optical density versus exposure time for a family of curves produced at different temperatures. This chart shows that maximum color development at 100° C. requires a dwell time approaching fifteen minutes within the reactor. However, equivalent development may be realized by heating the mixture to higher temperatures for shorter periods of time, for example, one minute at 135° C.

Figure 3:
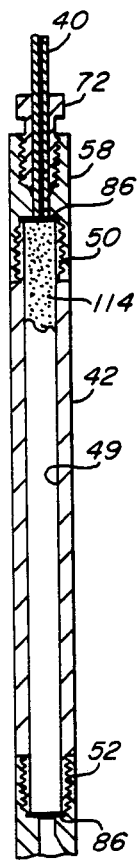
FIG. 3 is a side elevation view of the column reactor.

Attention is directed to FIG. 3 showing the reactor 42 which is an elongated straight tube preferably made of stainless steel or other corrosive resistant metals and an internal bore or chamber 49 throughout its length. The tube has threaded ends 50 and 52 establishing an entry and an exit port for the chamber 49. Each of the threaded ends 50 and 52 interface with a fitting 58 shown in detail in FIG. 4. The fitting 58 has a reactor tube receptacle end 60 and a flow line receptacle end 62. The interior of the tube receptacle end 60 has an internal threaded cavity 64 for engagement with the threaded end 50 of the reactor 42. The flow line receptacle end 62 of the fitting 58 has an internal threaded cavity 68 for connection with a threaded connector screw 72. The center of the connector screw 72 has a bore 76 which is designed to receive the capillary line 40 which is in fluid communication with the mixing tee 30 as shown in FIG. 2.

Figure 4:
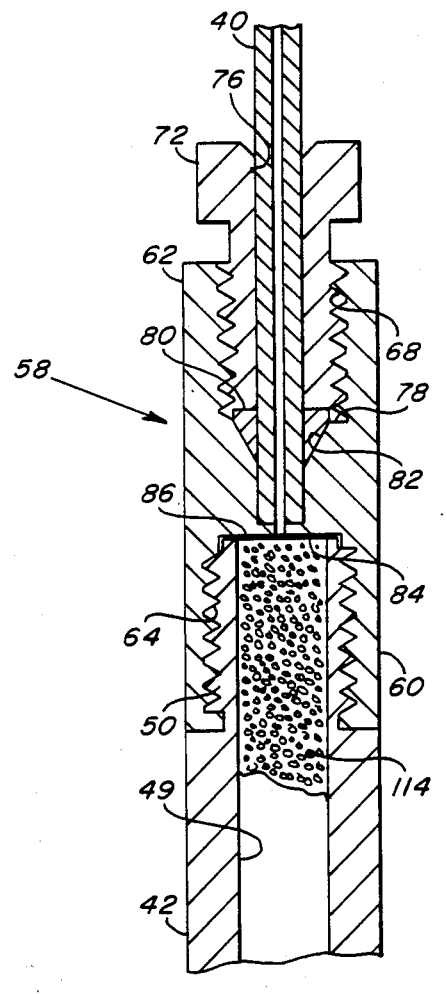
FIG. 4 is a sectional view of the fitting on one end of the column.

Adjacent the bottom 78 of the internal threaded cavity 68 of the fitting 58 in FIG. 4 is a ferrule 80 which is designed to engage with the frustoconical recess 82 in the bottom 78 of the fitting flow line end 62. The ferrule 80 provides sealing of the capillary line 40 to the fitting 58. Movement of the connector screw 72 toward the bottom 78 of the cavity will deform the metal ferrule and establish a tight seal.

Figure 5:
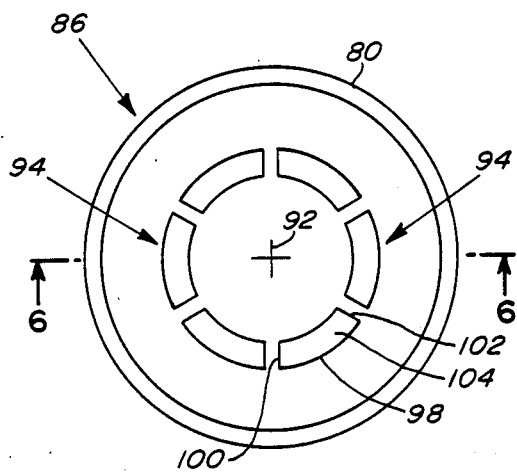
FIG. 5 is a top view of the retaining plate of the present invention.

Located adjacent the bottom 84 of the cavity 64 in the column end 60 of the fitting is a retaining plate or disc 86 which is held in place by the edge 88 of the threaded end 50 of the reactor 42. Attention is directed to FIG. 5, showing in more detail the retaining plate 86 which has an annular solid portion 90 that is designed to provide a seal between the fitting 58 and the edge 88 of the threaded end 50 of the tube reactor. Located in a circular array around the center 92 of the retaining plate 86 are a plurality of horizontally offset arcuate slots 94 which have openings small enough to retain the column packing particles which are placed within the reactor chamber, but are large enough to permit passage of the chromatographic effluent from the capillary path 40.

As shown in FIGS. 3 and 4, the reactor 42 has an internal bore or chamber 49 in which is placed a plurality of uniform packing material such as diamond grit which has an approximate seventy micron size. It should be noted that diamonds have very high thermal conductivity which leads to very uniform heating. This packing is placed in uniformity within the chamber 49 to ensure a uniform velocity profile across the column section. The uniform arrangement of the packed particles will establish small passages which in total are smaller in cross section than the cross section of a capillary coil. The flow path created by these particles is significantly longer than the length of the reactor chamber 49. The uniform arrangement in conjunction with the continual flow of the stream into the reactor will promote uniform travel or velocity of the stream throughout the cross section of the packed reactor bore, i.e., a uniform velocity profile.

It should be noted that the reactor 42 for use in an amino acid analyzer application is, for example, 0.250 inches in diameter and approximately 2.4 inches long with a bore 96 of approximately 0.125 inches. Also, the interior surface of the chamber 49 is treated by electroplating a noble metal such as platinum onto its surface.

Figure 6:
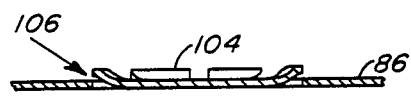
FIG. 6 is a sectional view taken along the lines 6—6 in FIG. 5.
Figure 7:
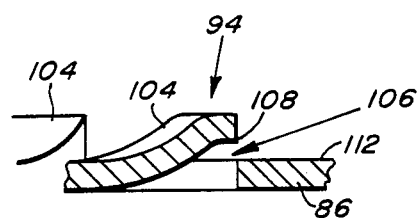
FIG. 7 is an enlarged partial sectional view of FIG. 6.
Figure 10:
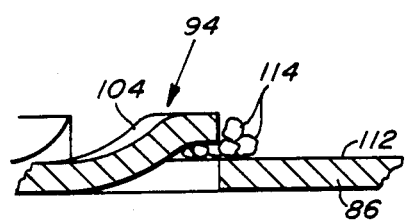
FIG. 10 shows an enlarged partial sectional view of the retaining plate illustrating the retention of the small packing particles.

Attention is directed to FIGS. 5-7, showing in more detail the retaining plate 86 of the present invention. Briefly, the slots 94 are formed by piercing the flat plate 86 along the outer arcuate edge 98 and the two radial edges 100 and 102 of each slot. The lip 104 formed by piercing of the plate 86 is bent out of the plane of the flat disc 86 to form the horizontally offset opening 106 of the slot. As shown more clearly in FIG. 7, the width of the slot is the distance between the bottom edge 108 of the front face 110 of the lip 104 and the adjacent surface 112 of the flat plate 86. The opening 106 between the edge 108 of the lip 104 and the surface 112 of the plate must be smaller than the diameter of the smallest particles used for the packing material in the reactor. As shown in FIG. 10, the size of the opening in the slot is critical to retain or retard the escape of any of the particles 114. The loss of any particles would create undesirable voids in the reactor chamber 49 which would be detrimental to the operation of the analyzer system. The lip 104 of each slot 94 projects into the chamber 49.

The length of the slots 94 is the distance between the respective radial edges 100 and 102. Therefore, the total opening for the flow of stream through each slot is the length of the slot times the width of the slot in addition to the small area adjacent the radial edges 100 and 102 of the slot. This total opening of all the slots 94 is equivalent to a large plurality of apertures or holes in the plate.

Although not precisely represented in the drawings, the opening 106 or distance between the edge 108 in FIG. 7 and the surface 112 is less than the thickness of the plate 86. By way of example, if the particle size being used for the packing has as its smallest diameter approximately 0.002 inches, the opening in the slot would be 0.0015. As stated previously, the thickness of the plate 86 is preferably 0.003 inches.

Typically, when the slotted discs 86 are made, the slots are not as clean and uniform as implied by the drawings and are somewhat jagged or irregular due to the high ductility of pure platinum. In order to ensure that the slots have been formed and are not blocked by these irregularities, the initial calculated deformation for punch-piercing and forming is typically exceeded. For example, with respect to a slot height of 0.0015 inches with a 0.003-inch thick platinum plate, the punch projections are made 0.007 inches long and the resulting punched piece measures 0.010 inches in height. After initial punching, to assure the formation of all sheared openings, the plate is repressed to a height of 0.0075 inches. This results in slots with a maximum opening of 0.0015 inches, so that none of the 0.002-inch Stoke's equivalent diameter diamond packed particles can pass.

In an instance where it may be desirable to retain even smaller diamond or other packing material, it is not possible to simply repress the offset lip of the slot to form a smaller opening, because the slot essentially will reclose almost completely because of the ragged and irregular edge caused by the initial shearing operation. One approach has been devised in the present invention to form or adjust the slots to provide uniform openings of essentially any desired dimension.

Figure 8:
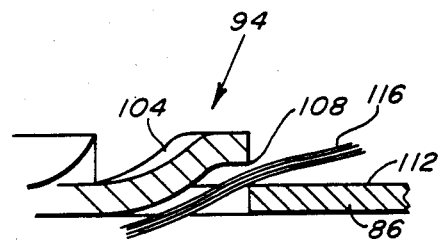
FIG. 8 shows an enlarged partial sectional view of the retaining plate showing one step in the method for precisely adjusting the width of the slot.
Figure 9:
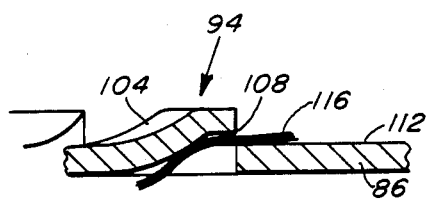
FIG. 9 is a view similar to FIG. 8 showing another step in the process of adjusting the slot width.

Once the slot has been formed to the general position as shown in FIG. 7, wherein the lip 104 has been separated out of the plane of the plate 86, it may be desirable to adjust the opening 106 between the edge 108 and the surface 112. One precise method of acccomplishing the desired opening is shown in FIG. 8, wherein the strip of shim stock or other uniform thickness material 116 having a width approximately the same as the length of the slot is placed into the opening 106. The lip 104 is pressed down against the shim stock 116 to establish the desired opening size. The result in position of the lip 104 is shown in FIG. 9 engaging the shim stock 116. Since the shim stock is preferably made of a relatively hard and polished material, it can be physically removed intact and reused.

In certain instances, it may be desirable to use shim material that can be easily removed chemically after the proper positioning of the lip 104. Possibly material such as brass or copper could be used and removed by dissolving in nitric acid. Similarly, aluminum foils are readily dissolved in sodium hydroxide solution. Another approach to establishing the necessary opening would be to pre-electroplate the platinum plate 86 prior to the formation of the slots. Pre-electroplating of the platinum could be done with a dissolvable material such as copper. Subsequently, the copper can be dissolved and the desired slot opening established.

Although the present invention shows the use of a flat thin plate for retaining the packed material within the reactor chamber, it is anticipated that other approaches could be utilized and obtain the same desired result. The plate, for instance, may be nonflat and could have other designed arrays of slots rather than the arcuate shape as shown in the accompanying drawings. For instance, the slots could be radially extending outward from the center of the plate, or they could be in oblique orientation with each other. Similarly, the slots could be of any particular desired length and opening size, providing they are formed generally so that the final size is adjusted by repressing as explained above to accommodate particle size and the amount of flow desired.

Another approach within the concept of this invention is the use of shims other than flat shim stock for the final pressure forming of slots. For example, a spaced parallel array of wires, such as fine tungsten wire, could serve to form very fine side-by-side holes by withdrawing them after pressing the lip of the slot closed against them.

What is claimed is:

1. A method of forming slots of a predetermined width in a material-retaining plate, said method comprising the steps of:
    perforating said plate in a pattern defining a selected array of slots and bending a portion of said plate within each set of slots laterally from the plane of said plate to form openings in said plate;
    placing a material of uniform thickness within each of said openings, said material having a thickness substantially equal to a predetermined width;
    re-bending said portions of said plate toward the plane of said plate to engage said material and pressing each of said portions against said material to form a slot having a width approximating the width of said material; and
    removing said material from said plate.

2. A method as defined in claim 1 wherein said material-placing step comprises placing a selectively dissolvable material within said openings and said removing step comprises dissolving said material.

3. The method as defined in claim 1 wherein said first step comprises perforating said plate in a pattern defining a circular array of openings.

4. A method of forming slots of a predetermined width in a thin plate, said method comprising:
    coating said plate with a dissolvable material, said coating having a specified thickness;
    perforating said plate in a pattern defining a selected array of slots and bending a portion of said plate within each set of slots laterally from the plane of said plate by a selected amount such that the outer edge of said portion extends over said plate; and
    re-bending said portions of said plate toward the plane of said plate to engage said dissolvable materials and pressing each of said portions to form a slot having a width approximating twice the width of said material; and
    dissolving said dissolvable material from said plate (to establish the slots of a predetermined width).

* * * * *

UNITED STATES PATENT AND TRADEMARK OFFICE
CERTIFICATE OF CORRECTION

PATENT NO. : 4,686,752

DATED : August 18, 1987

INVENTOR(S) : Thomas D. Sharples

It is certified that error appears in the above-identified patent and that said Letters Patent is hereby corrected as shown below:

On the face of the patent under the section titled "Related U.S. Application Data":

After "Division of Ser. No. 628,928, Jul. 9, 1984, abandoned"

Add: "which is a Continuation of Ser. No. 392,107, filed June 25, 1982".

Signed and Sealed this

Twenty-sixth Day of January, 1988

Attest:

DONALD J. QUIGG

*Attesting Officer*   Commissioner of Patents and Trademarks